(12) United States Patent
Van Herpen et al.

(10) Patent No.: US 8,039,818 B2
(45) Date of Patent: Oct. 18, 2011

(54) SUB WAVELENGTH APERTURE

(75) Inventors: Maarten M. J. W. Van Herpen, Eindhoven (NL); Derk J. W. Klunder, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 206 days.

(21) Appl. No.: 12/519,800

(22) PCT Filed: Dec. 18, 2007

(86) PCT No.: PCT/IB2007/055208
§ 371 (c)(1),
(2), (4) Date: Jun. 18, 2009

(87) PCT Pub. No.: WO2008/075289
PCT Pub. Date: Jun. 26, 2008

(65) Prior Publication Data
US 2010/0072397 A1 Mar. 25, 2010

(30) Foreign Application Priority Data
Dec. 21, 2006 (EP) .................................... 06126760

(51) Int. Cl.
*G01N 21/64* (2006.01)
(52) U.S. Cl. ............... 250/459.1; 250/458.1; 250/461.1; 250/461.2
(58) Field of Classification Search ............... 250/458.1, 250/459.1, 461.1, 461.2
See application file for complete search history.

(56) References Cited

U.S. PATENT DOCUMENTS

| | | | |
|---|---|---|---|
| 6,485,703 B1 * | 11/2002 | Cote et al. | 424/9.1 |
| 2003/0036204 A1 | 2/2003 | Stark et al. | |
| 2003/0132392 A1 * | 7/2003 | Kuroda et al. | 250/397 |
| 2005/0244863 A1 | 11/2005 | Mir | |
| 2006/0011862 A1 * | 1/2006 | Bernstein | 250/461.2 |
| 2006/0209413 A1 | 9/2006 | Kim et al. | |
| 2006/0234367 A1 * | 10/2006 | Schultz et al. | 435/199 |

FOREIGN PATENT DOCUMENTS
EP 1607737 A1 12/2005

OTHER PUBLICATIONS

Yuan et al: "Initial Demonstration of a Local, Evanescent, Array Coupled Biosensor Concept"; Sensors, 2005 IEEE, pp. 908-911.
Butkus, B.: "Quantum Dots Lend Simplicity"; Biophotonics International, vol. 11, No. 5, pp. 34-40.

* cited by examiner

*Primary Examiner* — David Porta
*Assistant Examiner* — Hugh Maupin

(57) ABSTRACT

There is provided a method of detecting a presence of a luminophore in a detection volume comprising providing excitation radiation in said detection volume. A luminophore is provided in said detection volume being excitable by said excitation radiation. The luminescent radiation is detected to identify the presence of said luminophore in said detection volume. In one aspect of the invention, said luminophore is selected to emit luminescent radiation having a wavelength in said medium that is larger than twice said smallest dimension; and wherein said luminophore is selected to be excitable by excitation radiation having a wavelength in said medium that is smaller than twice said smallest dimension. Accordingly, luminescent radiation is blocked from entering the detector but for the portion present on an interface of the aperture.

20 Claims, 5 Drawing Sheets

SUB WAVELENGTH APERTURE

FIELD OF THE INVENTION

The invention relates to the field of detecting a presence of a luminophore in a detection volume.

BACKGROUND OF THE INVENTION

US2005244863 discloses a configuration for excitation of luminophores by means of an evanescent wave. An evanescent wave is a rapidly decaying electromagnetic field which cannot propagate due to a sub-wavelength aperture. In this disclosure, exciting radiation is provided to penetrate as an evanescent wave in a bio-molecule containing mixture. The evanescent wave is created by a structure having sub wavelength apertures. However, the apertures only allow a small portion of the generated radiation to be transmitted. This causes a limited yield of luminescent light to be used for detection purposes.

SUMMARY OF THE INVENTION

A desire hence exists to increase the yield of luminescent radiation. Accordingly, in one aspect of the invention, there is provided a method of detecting a presence of a luminophore in a detection volume, comprising: providing excitation radiation in said detection volume; providing a luminophore in a medium in said detection volume, the luminophore being excitable by said excitation radiation to emit luminescent radiation; and detecting at least a polarization component of said luminescent radiation through an aperture of said detection volume by a detector, said aperture having a smallest in plane dimension; wherein said luminophore is selected to emit luminescent radiation in said medium having a wavelength in said medium that is larger than twice said smallest dimension; and wherein said luminophore is selected to be excitable by excitation radiation having a wavelength in said medium that is smaller than twice said smallest dimension.

In another aspect of the invention there is provided an apparatus for detecting a presence of a luminophore in a detection volume, comprising: a detection volume; the detection volume comprising an aperture having a smallest in plane dimension and arranged to comprise said luminophore in a medium; a radiation source for providing excitation radiation in said detection volume, the luminophore being excitable by said excitation radiation to emit luminescent radiation; and a detector arranged and constructed to detect at least a polarization component of said luminescent radiation said detector is selected to detect luminescent radiation having a wavelength in said medium that is larger than twice said smallest dimension; and wherein said radiation source is selected to provide excitation radiation having a wavelength in said medium that is smaller than twice said smallest dimension.

In one aspect of the invention, the aperture defines an in plane interface where a luminophore can be excited. Instead of limiting an excitation volume by using an evanescent tail of excitation light, here, the detection volume can be limited, by detecting fluorescence light that is created on the interface of the aperture. Accordingly, the excitation efficiency can be improved; while keeping the detection volume limited. These and other aspects of the invention will be apparent from and elucidated with reference to the embodiment(s) described hereinafter.

DETAILED DESCRIPTION OF EMBODIMENTS

Figure 1:
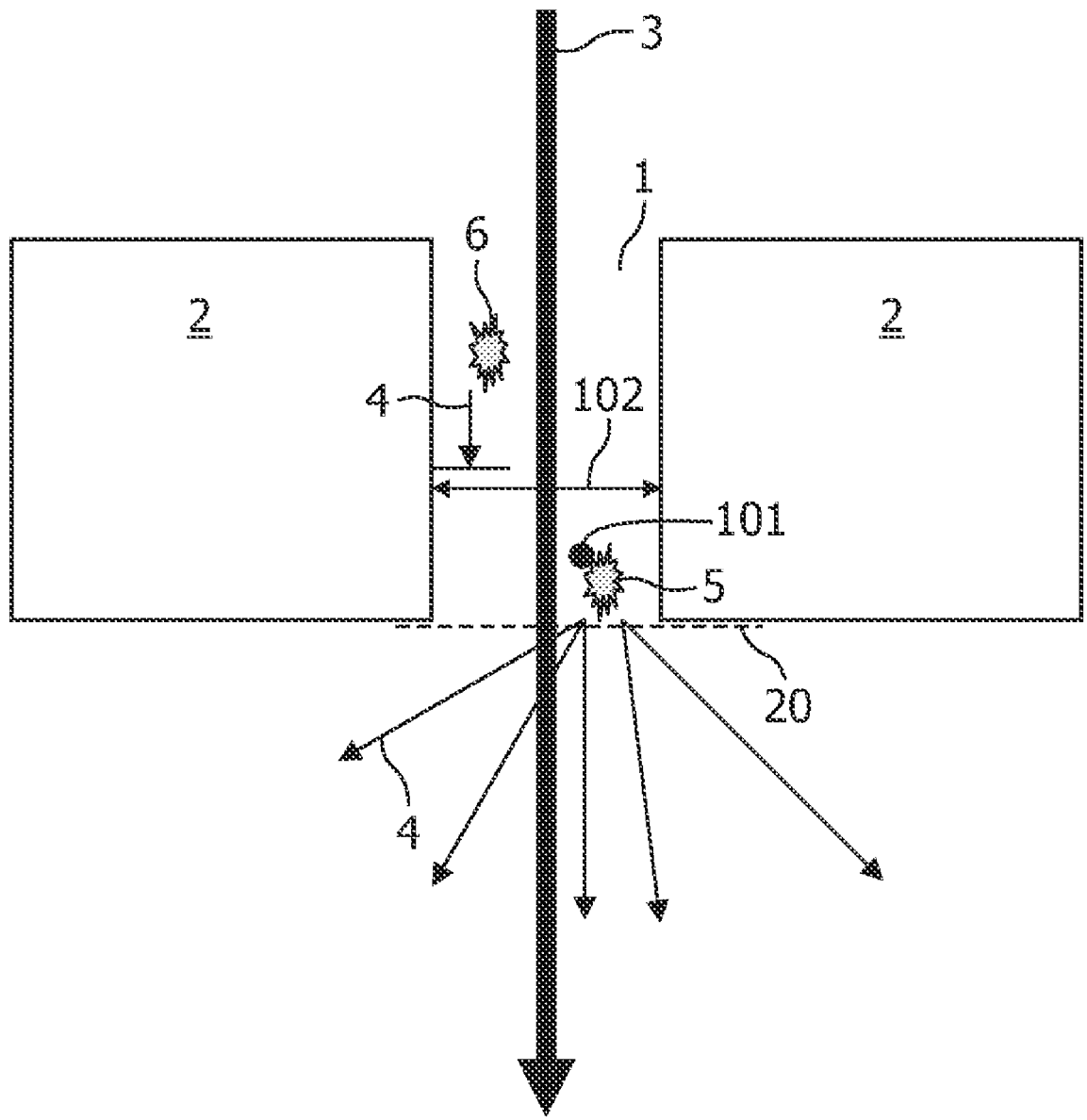
FIG. 1 illustrates a basic embodiment according to an aspect of the invention.

In the art, aperture biosensors are used for detecting luminophores, such as fluorophores, to identify specific types of bio-molecules that are being investigated. Generally these apertures use a pin-hole or slit concept to allow excitation light as evanescent radiation into a detection volume. However, for an aperture biosensor the combined effect of the excitation and fluorescence detection efficiency significantly reduces the total efficiency of the biosensor. A secondary problem is that in the particular case of a pinhole biosensor in transmission mode the total efficiency is the same over the entire dept of the biosensor. Preferably, the total efficiency is higher in certain parts, because that effectively will give a smaller excitation/detection volume. In one aspect, the invention proposes a sub-wavelength aperture to limit only the detection volume. This can be achieved by using luminophores with a very large wavelength difference (stokes shift) between excitation and fluorescence in combination with a aperture (bio)sensor. In this way, excitation light can enter substantially unhindered through the aperture 1 of the detection volume, significantly increasing the effectiveness of the excitation. Said luminophore is selected to emit luminescent radiation having a wavelength so that the luminescent radiation generates an evanescent field inside the aperture. Accordingly, luminescent radiation is blocked from escaping the aperture 1 except for the portion present on an interface 20 of the aperture 1 so that the detection volume 101 is kept small to reduce the effect of background fluorescence and thus increase the selectivity of the detection by improving the signal-to-noise ratio of the biosensor. In another aspect of the invention, to improve excitation and detection efficiency, a slit can be used instead of a hole. The advantage of using a slit is that the suppression becomes polarization dependant, and due to this 50% of the generated fluorescence can exit the slit without being suppressed.

In an aspect of the invention, a smallest dimension of the aperture is selected to be larger than one half of the excitation light wavelength in said medium; and smaller than one half of the wavelength in said medium of the luminescent light emitted by a luminophore to be excited by the excitation light. In this respect, the type of luminophore that is used is selected to be excitable by radiation having a wavelength in said medium substantially smaller than twice the smallest aperture dimension; while emitting luminescent light substantially larger than the twice the smallest aperture dimension, so that luminescent radiation is trapped within the aperture except for the luminescence that is created substantially on the interface 20 of the aperture. Specifically, the interface 20 is formed by an outer plane defined by the aperture 1, when seen in a traveling direction of the fluorescent light 4.

Accordingly, in one aspect, the current invention proposes the use of luminophores that have (very) large wavelength difference (stokes shift) between excitation and fluorescence. For this purpose one can use for example luminophores such as quantum dots (ref. "Quantum Dots Lend Simplicity", B. D. Butkus, Biophotonics International, pp. 34-40, May 2004). For example, such a quantum dot may be illuminated with a wavelength of 330 nm and it may give emission fluorescence at 610 nm. However, this emission fluorescence can also be varied, to allow multiplexing with different fluorescence emission wavelengths (for example, excitation at 330 nm and emission at 510, 555, 590 and 610 nm, allowing 4 analytes to be measured simultaneously). Another example of luminophores with a large Stokes shift are LaF3:Nd nanoparticles. These nanoparticles are composed of Lanthanum Fluoride (LaF3) crystals with about 5% of the Lanthanum ions (La3+) replaced by Neodymium ions (Nd3+). These nanoparticles have typical diameters of 6 nm and prevent quenching of the excited states. Each nanoparticle consists of 60 Neodymium ions, 1200 Lanthanum ions and 3780 Fluoride ions (F−). Pumping at a wavelength around 575 nm results in emission around wavelengths of 880 nm, 1050 nm, and 1330 nm.

In FIG. 1 a basic embodiment according to the invention is outlined, showing an aperture 1 within a material 2. In the figure, the aperture 1 defines a width 102 as a smallest in plane dimension, of an interface plane 20 normal to the paper defining a lower side of detection volume 101. Detection volume 101 is further bounded by the aperture width 102. The size of the aperture 1 is large enough to allow excitation radiation 3 to travel through the aperture essentially without being suppressed. In particular, the luminophore 5 is selected to be excitable by excitation radiation 3 having a wavelength in said medium that is smaller than twice said aperture width 102. However, fluorescence 4 generated by fluorophores 5 and 6 is being suppressed, because the fluorescence wavelength is substantially larger than the aperture width 102. Due to this, the detection volume 101 is limited, at least for fluorescence 4 that is polarized in a direction transverse to the width 102 of the aperture. Fluorescence 4 generated by a fluorophore 5 located near the interface 20 (independent of polarization) can leave the aperture 1 and reach a detector (not shown). Fluorescence 4 generated further into the aperture 1, for example by fluorophore 6 is suppressed before it can reach the exit of aperture 1 since the fluorophore 6 is selected to emit luminescent radiation in having a wavelength in said medium that is larger than twice said smallest dimension. This is an advantage, because for example in a biosensor assay the signal fluorophores may be bound to capture probes within the detection volume 101, such that fluorophores 6 are background particles, while the fluorophore 5 is a signal particle. A filter may be provided (not shown) that blocks the excitation and transmits the fluorescence radiation 4, so that the excitation radiation 3 can be prevented from being detected by a detector.

In a preferred embodiment, the width 102 of the smallest dimension of the aperture 1 is such that:
  excitation light 3 is able to travel through the aperture 1 without being (substantially) suppressed;
  fluorescence light 4 is substantially suppressed, at least in a dimension defined by the aperture width 102 when traveling through the aperture 1.

The above conditions can be met when the size of the aperture is greater than the diffraction limit in said medium of the excitation radiation and when the size is at the same time smaller than the diffraction limit in said medium of the fluorescence radiation (note that this diffraction limit depends on the index of refraction of the medium that is filling the apertures).

In one example the excitation wavelength is 575 nm and the generated fluorescence is at 880 nm; having the aperture filled with water having an index of refraction of 1.3. Using an aperture with a smallest dimension of 250 nm and an aperture depth of depth of 400 nm calculation can show that this will result in a transmission of the excitation light of about 84.4% and a transmission of the fluorescence of about 0.7% when traveling through the entire aperture.

Figure 2:
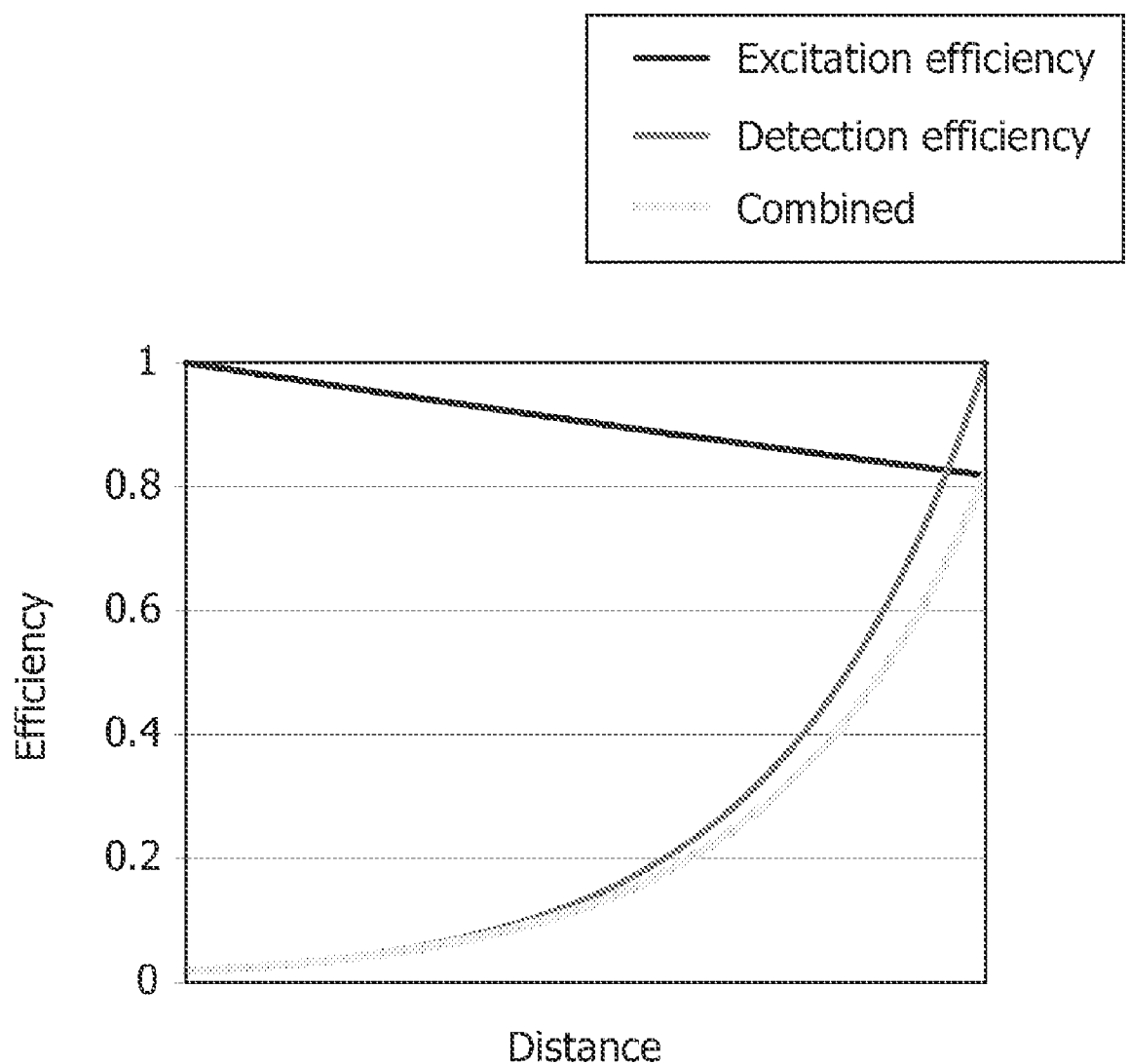
FIG. 2 illustrates a combined effect of excitation and fluorescence detection efficiency.

FIG. 2 shows the combined effect of excitation and fluorescence detection efficiency, for a configuration typically as in FIG. 1; that is, with excitation light traveling into the aperture 1. The x-axis shows in arbitrary units a depth parameter of the aperture 1, wherein the efficiency of the excitation radiation 3 is shown to be generally unhindered while traveling through the aperture 1, giving a minor decrease in excitation efficiency with distance; the typical efficiency lowering from 1 to 0.8. However, the fluorescence 4 having a wavelength typically larger than the aperture 1, is accordingly strongly suppressed by the aperture 1, and therefore the detection efficiency increases near the exit of the aperture. It is noted that in this case the aperture is used in transmission mode. When combined, the total efficiency is still high, limited only substantially by the fluorescence detection efficiency. Since the fluorescence detection decreases with distance, seen from the exit of the aperture, that is, the end through which the luminescent radiation escapes prior to being detected a small detection volume is provided which is formed by substantially a volume between the aperture just before the exit of the aperture, and accordingly only comprises a limited number of luminophores.

In the inventive embodiment, as can be seen from this figure, the excitation/detection volume is limited by the detection volume the since only fluorescence 4 near the exit can leave the aperture 1.

Figure 3:
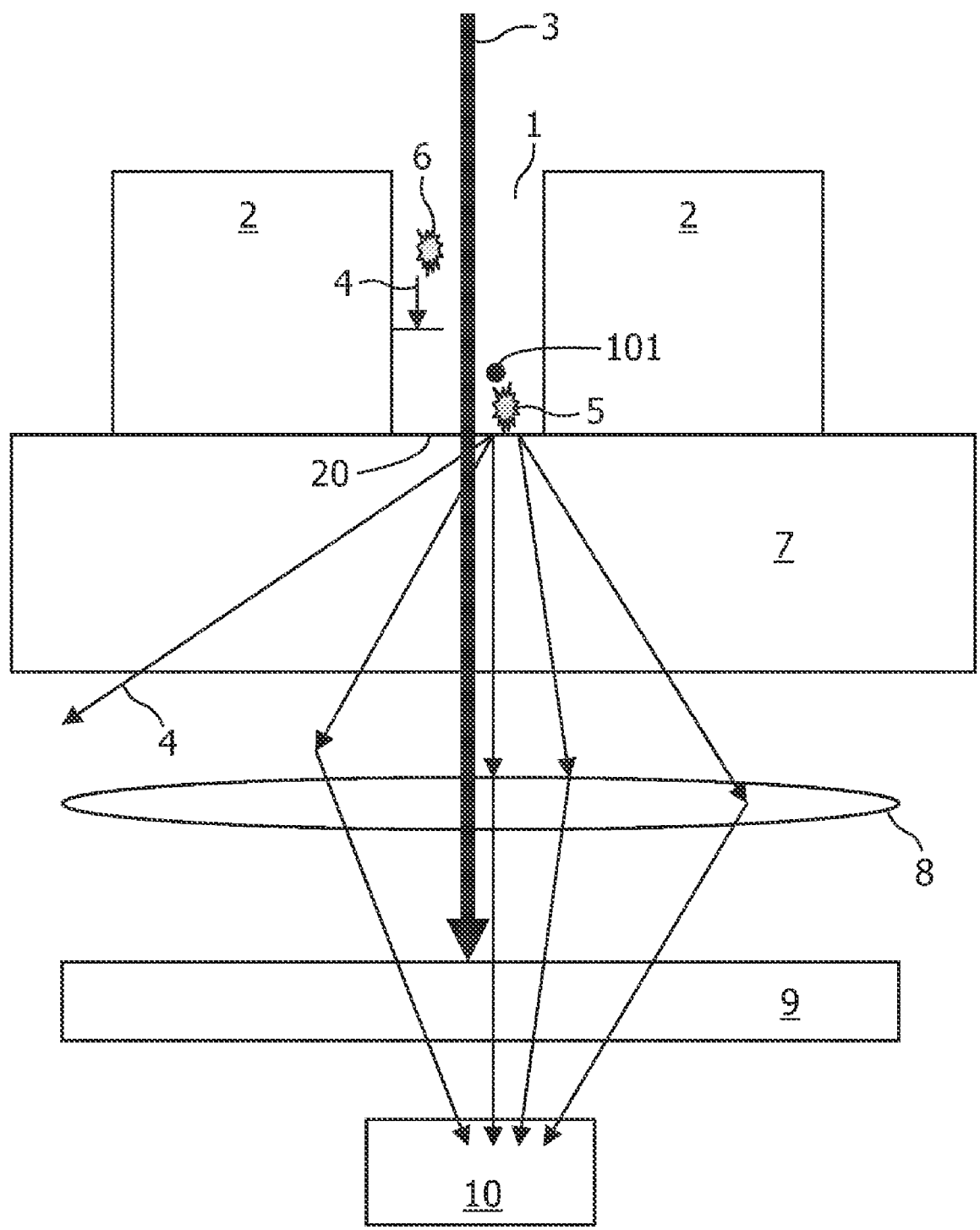
FIG. 3 illustrates a transmissive detection of luminescent radiation according to an aspect of the invention.

FIG. 3 show an embodiment wherein a substrate 7, such as a glass plate, is positioned at the interface 20 of the aperture 1. Accordingly, a top layer of the glass plate 7 forms interface 20, that prevents the fluorophores 5, 6 from being present in an in between volume between a detection volume 101 and detector 10. Thus, excitation radiation 3 in an in between volume between the detection volume 101 and the detector 10 cannot contribute to excitation of fluorophores since, no fluorophores are present between the detector and the interface 20 of the aperture (on detector side). In this way inadverted illumination of fluorophores by the excitation beam which would contribute to a background fluorescence signal is prevented. Thus, in a preferred embodiment of this invention a glass plate 7 is used as substrate for the apertures (instead of the embodiment shown in FIG. 5 that has no substrate beneath the apertures). This is shown in FIG. 3, which shows a substrate 7 beneath the aperture. The figure also shows a lens 8 that is used to focus the fluorescence onto a detector 10. A detection filter 9 is used to block the remaining excitation radiation.

An additional advantage of the substrate 7 is that fluorophores can bind to the glass surface within the aperture, positioning the fluorophores in the location with the highest total efficiency of excitation+detection.

Although the embodiment of FIG. 3 is used in transmission mode, alternatively, in another embodiment, the aperture 1 may be used in reflection mode. For this case, the combined efficiency of excitation and detection is similar to the transmission mode embodiment that was discussed with reference to FIG. 2. In such a reflective embodiment, the excitation beam can illuminate the apertures through the glass plate 7.

Figure 4:
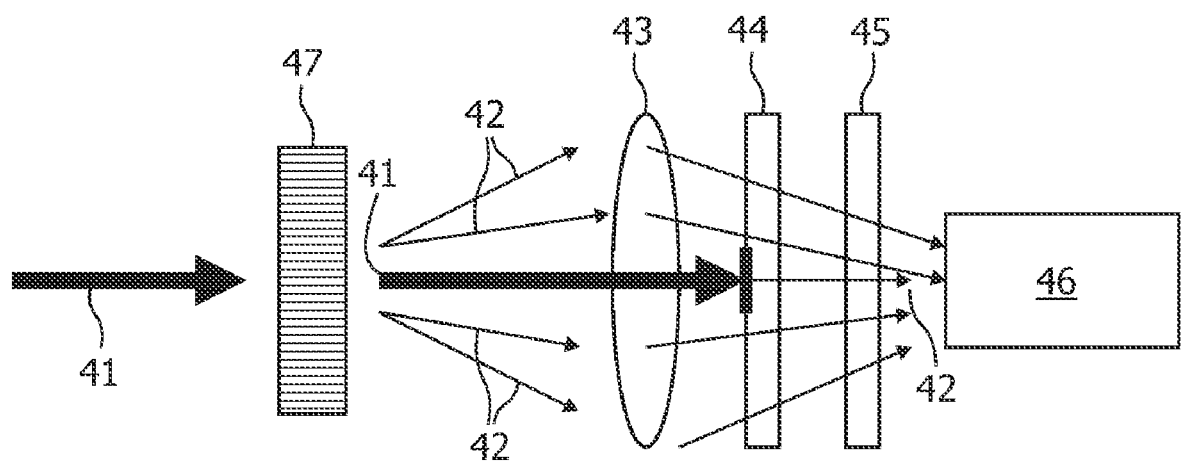
FIG. 4 illustrates an alternative embodiment according to an aspect of the invention using slits.
Figure 5:
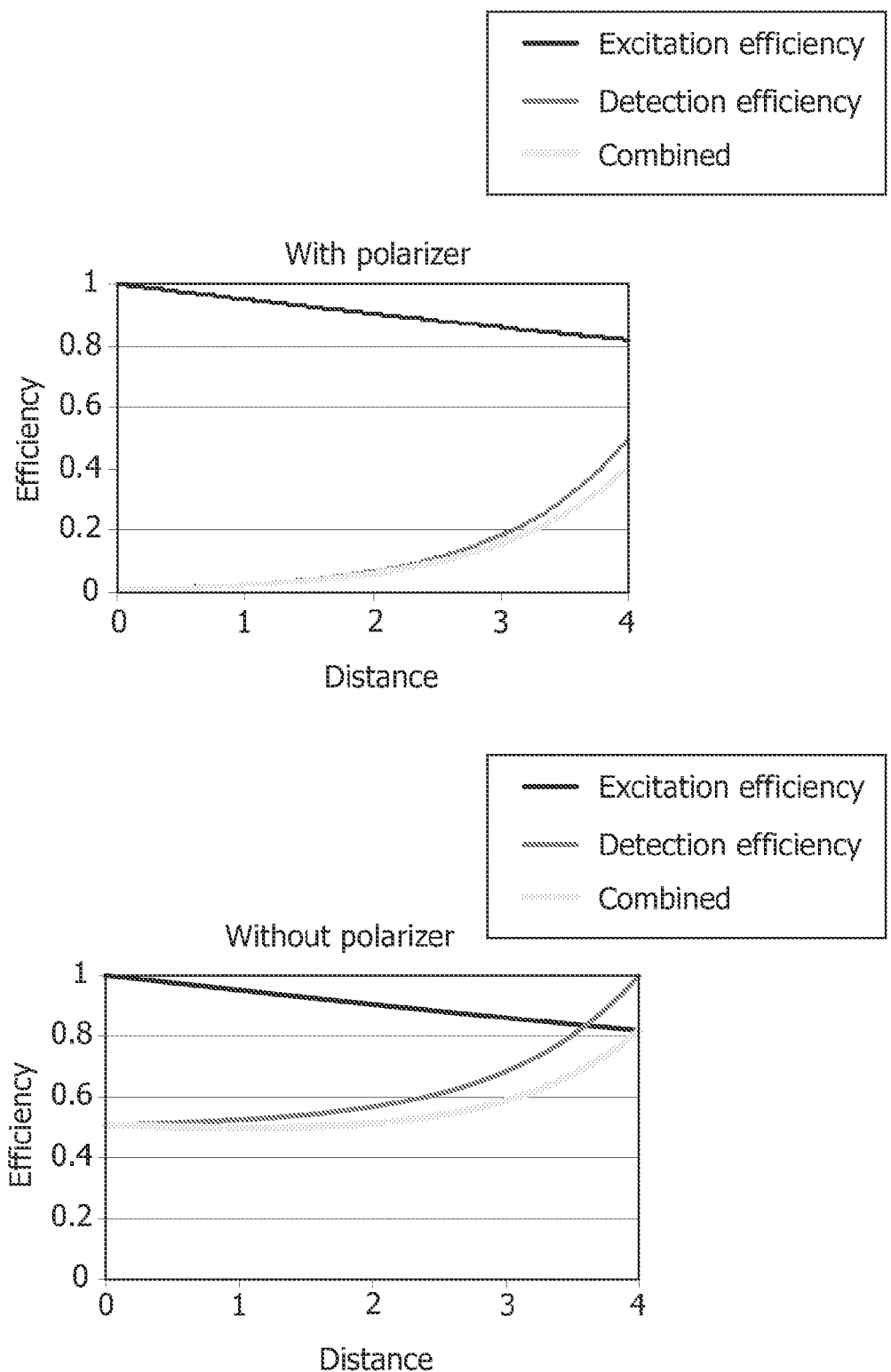
FIG. 5 illustrates a schematic graph showing a detection efficiency for the embodiment illustrated in FIG. 4.

Furthermore, in addition to the pinhole embodiments disclosed in FIG. 1 and FIG. 3 an embodiment can be used wherein the apertures are provided by slits 47 as shown in FIG. 4. While in the embodiment of FIG. 4 (background) fluorescence 42 having a polarization component parallel to the slit direction is prevented to escape the slits 47, in this embodiment, fluorescence 42 having a polarization (that is direction of the electric field) along said smallest dimension can travel through the apertures formed by slits 47 towards detector 46. To distinguish between background fluorescence generated anywhere in the slit and fluorescence generated at the end of the slit a polarization filter 45 may be used, to select only a component of the fluorescence generated at the end of the slit. The advantage of this embodiment is that it is possible to switch between a large and a small detection volume. FIG. 4 shows the embodiment for this case and FIG. 5 shows how the polarizer in front of the detector can be used to switch between a large and a small detection volume. In FIG. 4 a beam of excitation light (41) is illuminating the slits (47) (for example a wiregrid polarizer). The excitation radiation can travel through the slits without being substantially suppressed, because the (TE polarized) excitation wavelength is too short to be suppressed by the wiregrid, or because the excitation beam is TM polarized such that it is not suppressed by the wiregrid. A lens (43) placed behind the wiregrid is used to collect and focus the emitted fluorescence (42) onto a detector (46). Between the lens and the detector, a detection filter (44) (that blocks the excitation light) and a polarizer (45) are placed (note that the order of 43, 44 and 45 can be mixed). Preferably, the polarizer (45) can be either rotated, or it can be easily removed.

FIG. 5 shows the effect of removing the polarizer (45) behind the wiregrid. The figure at the top shows the combined detection+excitation efficiency with a polarizer behind the wiregrid, placed such that it blocks the polarization that would normally transmit through the wiregrid without being suppressed. In this case the maximum detection efficiency is 50%, because the polarizer will suppress at least 50% of the fluorescence. As can be seen in the figure, the detection volume is limited by the suppression of the fluorescence, yielding a small detection volume.

If desired, the detection volume can be increased by removing the polarizer. This results in the efficiency as shown in the lower image in FIG. 5, where can be seen that the total efficiency is high over the full distance. Instead of removing, it is also possible to rotate the polarizer by 90 degrees, but this in this case the total efficiency is roughly 50% lower. Alternatively, one may choose to rotate the polarizer continuously, in order to take advantage of both states.

If the embodiment in FIG. 4 is only used for achieving a small detection volume, it is possible to remove the detection filter (44) completely, because in this case the polarizer 45 will block all light that is polarized such that it can travel through the slits without being suppressed (and this can include the excitation light).

Note that also for this embodiment, preferably there is a glass plate (not shown) on the detection side of the slits, in order to prevent background signals to be generated between the aperture exit and the detector.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein fluorescence is used as a marker or as a tracer for biomedical purposes.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of detecting a presence of a luminophore in a medium, the method comprising:
   providing excitation radiation to a detection volume formed in an aperture extending through a material, the detection volume being positioned at an exit of the aperture and defined, in part, by an aperture width corresponding to a smallest in plane dimension of the aperture;
   providing the luminophore in the medium in the detection volume, the luminophore being excitable by the excitation radiation to emit luminescent radiation; and
   detecting at least a polarization component of the luminescent radiation emitted through an exit of the aperture,
   wherein the luminophore is selected to emit luminescent radiation having a wavelength in the medium that is larger than twice the aperture width, and the luminophore is selected to be excitable by the excitation radiation having a wavelength in the medium that is smaller than twice the aperture width, and
   wherein the detection volume is further defined by the wavelength of the luminescent radiation, in that detection of luminescent radiation emitted by a luminophore not in the detection volume is suppressed by the aperture width.

2. The method according to claim 1, wherein said detection volume is selected to comprise a limited number of luminophores.

3. The method according to claim 1, wherein said luminophore is selected from the group of quantum dots and LaF3:Nd particles.

4. The method according to claim 1 further comprising:
   preventing said excitation radiation from being detected.

5. The method according to claim 1 further comprising:
   preventing said excitation radiation from exciting luminophores in an in between volume located between the detection volume and a detector for detecting the polarization component of the luminescent radiation.

6. The method according to claim 5, wherein said luminophores are prevented from being present in said in between volume.

7. The method according to claim 1, wherein said luminophore is arranged to bond with a biomolecule.

8. The method according to claim 1, wherein said excitation radiation is polarized.

9. An apparatus for detecting presence of luminophores in a medium, the apparatus comprising:
   a detection volume containing the medium and formed in an aperture extending through a material of the apparatus, the detection volume being positioned at an exit of the aperture and defined, in part, by an aperture width corresponding to a smallest in plane dimension of the aperture;
   a radiation source configured to provide excitation radiation to the detection volume through the aperture, causing luminophores in the detection volume to emit luminescent radiation from the exit of the aperture, the excitation radiation having a wavelength in the medium that is smaller than twice the aperture width; and a detector configured to detect the luminescent radiation emitted from the exit of the aperture having a wavelength in the medium that is larger than twice the aperture width, wherein the detection volume is further defined by the wavelength of the luminescent radiation, in that detection of luminescent radiation emitted by luminophores not in the detection volume is suppressed by the aperture width.

10. The apparatus according to claim 9, wherein said radiation source and said detector are provided in a transmissive configuration.

11. The apparatus according to claim 9, wherein said aperture is formed by one or more pin holes defining a largest in plane aperture dimension, wherein said largest in plane aperture dimension is smaller than a diffraction limit in said medium.

12. The apparatus according to claim 9, wherein said aperture is formed by one or more slits.

13. The apparatus according to claim 12, wherein said apparatus further comprises a polarizing filter used in conjunction with said one or more slits, so as to block part of the luminescent radiation.

14. The apparatus according to claim 13, wherein said polarizing filter is rotatable to selectively transmit luminescent radiation polarized by said one or more slits.

15. The apparatus according to claim 13 wherein said polarizing filter is provided between said one or more slits and said detector.

16. The apparatus according to claim 9, further comprising a blocking optical element to prevent said excitation radiation from being detected by the detector.

17. The apparatus according to claim 16, wherein said blocking optical element comprises a wavelength filter or polarizing filter.

18. The apparatus according to claim 16, wherein said blocking optical element is arranged to prevent said excitation light exiting from the detection volume.

19. The apparatus of claim 9, further comprising:

a substrate abutting the exit of the aperture, wherein at least one of the luminophores in the detection volume binds to a surface of the substrate.

20. The apparatus of claim 19, wherein the substrate comprises a glass plate.

* * * * *